United States Patent [19]

Kane et al.

[11] 4,196,303

[45] Apr. 1, 1980

[54] D-ISOMENTHOXYACETIC ACID

[75] Inventors: Bernard J. Kane, Atlantic Beach; Sean G. Traynor, Jacksonville, both of Fla.

[73] Assignee: SCM Corporation, New York, N.Y.

[21] Appl. No.: 890,622

[22] Filed: Mar. 20, 1978

[51] Int. Cl.$^2$ .................... C07C 61/38; C07C 69/74; C07C 103/737

[52] U.S. Cl. .............................. 560/126; 252/522 R; 260/557 R; 562/508

[58] Field of Search .................... 560/126; 562/508; 260/557 R

[56] References Cited

U.S. PATENT DOCUMENTS

| | | | |
|---|---|---|---|
| 2,044,968 | 6/1936 | Bruson | 562/588 |
| 3,715,382 | 2/1973 | Karady et al. | 560/34 |

*Primary Examiner*—Robert Gerstl
*Attorney, Agent, or Firm*—A. Joseph Gibbons; J. K. Mueller, Jr.

[57] ABSTRACT

The compound d-isomenthoxyacetic acid and various ester and amide derivatives are useful resolving agents and perfume ingredients.

4 Claims, No Drawings

D-ISOMENTHOXYACETIC ACID

BACKGROUND OF THE INVENTION

The present invention is directed to the novel compound d-isomenthoxyacetic acid.

It has been reported in the literature that d-menthoxyacetic acid and l-menthoxyacetic acid are useful resolving agents such as for d,l-cyclohexanediol, d,l-zearalenone 4-methyl ether, and d,l-menthol, for example. These menthoxyacetic acids are based on d-menthol and l-menthol, which are two of the eight isomers of menthol which have been reported in the literature. A good discussion of the menthols can be found in the publication *The Terpenes*, Volume 1, Part 1, Chapter 2, Pages 230-250, by J. L. Simonson, Cambridge at the University Press, 1947.

The instant invention is a new menthoxyacetic acid based on d-isomenthol. The instant d-isomenthoxyacetic acid potentially is a resolving agent and is useful as an intermediate in preparing odorants and fragrances.

BROAD STATEMENT OF THE INVENTION

The present invention is a novel compound d-isomenthoxyacetic acid and certain of its reaction products such as its menthyl ester, it ethyl ester, and its ethyl amide, for example. The preparation of d-isomenthoxyacetic acid involves the addition of an alkali metal to d-isomenthol followed by the addition of chloroacetic acid to the formed intermediate, an alkali metal d-isomenthoxide. The d-isomenthoxyacetic acid then is liberated by the addition of a protic acid, for example, and purified by conventional techniques.

DETAILED DESCRIPTION OF THE INVENTION

The novel compound of the present invention is d-isomenthoxyacetic acid which can be represented conventionally by the following generalized structure:

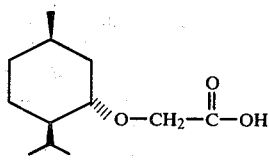

Its preparation is from d-isomenthol which can be prepared conveniently by stereoselectively hydrogenating d-trans-piperitol. Hydrogenation of d-trans-piperitol to d-isomenthol and hydrogenation of related cyclic allylic alcohols have been reported in the literature and the following list is representative of such reports:

1. "Synthesis of Laevo-menthol from a Citrus By-Product", J. C. Leffingwell and R. E. Shackelford, presented by Dr. Leffingwell at the annual Tobacco Research Chemists' Conference, Winston-Salem, N.C., on Oct. 5, 1973;
2. "Menthol, Part 4: Manufacturing Processes and Syntheses," by Dr. Siegfried Mignat and Fredrich Porsch, Dragoco Report, 1962, No. 1, 10-23 (Page 17);
3. "Reactions of Alpha, Beta-Unsaturated Cyclic Aldehydes and Ketones Part IX", A. Killen Macbeth and J. S. Shannon, *Journal of the Chemical Society*, 1952, 2852-2856;
4. "Reactions of Alpha, Beta-Unsaturated Cyclic Aldehydes and Ketones Part XI", A. Killen Macbeth, B. Milligan and J. S. Shannon, *Journal of the Chemical Society*, 1953, 901-902;
5. U.S. Pat. No. 3,028,418, Example No. 22 by Robert L. Webb;
6. U.S. Pat. No. 2,894,040 by Joseph P. Bain et al;
7. U.S. Pat. No. 2,935,526 by Joseph P. Bain.

The foregoing processes, however, suffer from incomplete stereoselectivity in formation of the desired d-isomenthol diastereoisomer over other possible diastereoisomers (or diastereoisomeric dl pairs) of the same carbon nucleus or structure. Thus, a preferred process for stereoselectively hydrogenating d-trans-piperitol to d-isomenthol is the Kane et al process disclosed in U.S. Pat. No. 4,058,572, the disclosure of which is expressly incorporated herein by reference. In this preferred process, the stereoselective hydrogenation utilizes a nickel hydrogenation catalyst that has an effective fraction of its reactive surfaces inactivated by treating said catalyst with an effective amount of a modifier selected from the group consisting of: an inorganic salt of a metal from Groups I through VIII, periods 4 through 7 of the Periodic Table, of the Rare Earths of the Periodic Table, and of aluminum; organic halides; hydrogen halides; and halo compounds of arsenic and boron. A preferred nickel hydrogenation catalyst for this process is a Raney nickel catalyst and preferred modifiers include nickel chloride and copper chloride. Hydrogenation conditions for this process are conventional.

The first step in preparing d-isomenthoxyacetic acid from d-isomenthol is the addition of an alkali metal thereto for formation of the corresponding alkali metal-d-isomenthoxide. This reaction conveniently is conducted in an organic solvent such as benzene, toluene, tetrahydrofuran or the like under reflux conditions for about 4 to 15 hours or longer. Preferably, the alkali metal is sodium, potassium, or lithium. Upon completion of this reaction any unreacted alkali metal preferably is separated from the reaction mixture. The next step in this process is the addition of monochloroacetic acid to the reaction mixture. This reaction is conducted in the organic solvent under reflux conditions for about 20 to 48 hours or thereabout to form the intermediate, alkali metal d-isomenthoxyacetate. This acid salt is recovered from the reaction mixture by conventional water washing or extraction techniques and then is acidified with a protic acid, such as hydrochloric acid or the like, to form the desired d-isomenthoxyacetic acid. The d-isomenthoxyacetic acid then can be recovered and purified by distillation, extraction with ether, methylene chloride or the like, or by some similar conventional technique. As an alternative to the chloroacetic acid addition step, a monochloroacetic acid ester can be added to the alkali metal-d-isomenthoxide to directly produce a d-isomenthoxyacetic acid ester. Such ester can be converted into d-isomenthoxyacetic acid in conventional fashion or can be used as a perfumery ingredient, for example, as shown below.

The instant d-isomenthoxyacetic acid is a potential resolving agent. Additionally, the d-isomenthoxyacetic acid can be converted into a variety of compounds which are useful as perfumery ingredients. Hence, ethyl d-isomenthoxy acetate has a peppery, woody odor; N-ethyl-disomenthoxyacetamide has an earthy, musty, fermented, sweet camphoraceous-like odor; and menthyl d-isomenthoxy acetate has a muted peppery, fruity, citrusy, spicy odor.

The following Examples show in detail how the present invention can be practiced but should not be construed as limiting. In this application all temperatures are in degrees Centigrade and all units are in the Metric System, unless otherwise expressly indicated.

EXAMPLE 1

Preparation of d-Isomenthoxyacetic Acid

To a 5 l. flask equipped with a mechanical stirrer, condenser, and addition funnel was added dry toluene (1 l.), d-isomenthol (2.56 moles), and sodium metal (2.6 gram-atoms). The reaction mixture was refluxed with stirring under nitrogen until all the sodium was reacted. Chloroacetic acid (1.0 moles) in toluene then was added slowly to the cooled reaction mixture. The reaction was exothermic and after the addition was complete, the reaction was refluxed for 48 hours. To the cooled solution was carefully added water (1 l.) and the organic layer was washed with two further portions of water. Separation of the toluene allowed the recovery of d-isomenthol which can be recycled. Acidification of the aqueous layer with HCl followed by extraction with diethyl ether (or methylene chloride) and evaporation of the dried organic extracts gave crude d-isomenthoxyacetic acid (0.58 moles) which can be further purified by distillation. b.p.=127°-130°/0.5 mm; $[\alpha]_D = +23.85°(C=20.8)$EtOH. Found: C, 67.47; H, 10.34; Calc. for $C_{12}H_{22}O_3$; C, 67.25; H, 10.35%.

EXAMPLE 2

Preparation of Ethyl d-Isomenthoxy Acetate d-Isomenthoxyacetic acid (0.096 moles) was refluxed in a round bottom flask (fitted with a condenser, a Dean-Starke water trap and a magnetic stirrer) containing toluene (100 ml), ethanol (0.13 moles), and concentrated sulfuric acid (1 drop). After refluxing for 15 hours and removal of water, the cooled reaction mixture was extracted with aqueous sodium carbonate and dried over magnesium sulfate. Evaporation and distillation of the oily residue (30 g.) gave ethyl d-isomenthoxy acetate as a colorless oil. b.p.=88°-92°/<1 mm. IR and NMR spectra were compatible with the ester.

EXAMPLE 3

Preparation of l-Menthyl d-Isomenthoxy Acetate d-Isomenthoxyacetic acid (0.234 moles) was refluxed for 17 hours in toluene (500 ml) containing l-menthol (0.25 moles), and p-toluenesulfonic acid (0.1 g.) Removal of water was provided for. The cooled reaction mixture was washed with sodium carbonate (100 ml), brine (100 ml), dried over magnesium sulfate, and evaporated to give an oil (78.6 g.) which by GLC analysis contained 85.9% ester and 9.3% l-menthol. Distillation gave the pure l-menthyl d-isomenthoxy acetate. b.p.=136°/0.35 mm. Found: C, 75.00; $H_{11.44}$. Calc. For $C_{22}H_{40}O_3$; C, 74.95; H, 11.44%.

EXAMPLE 4

Preparation of d-Menthyl d-Isomenthoxy Acetate

The procedure of Example 3 was repeated but with d-menthol (0.1 moles) instead of l-menthol. Distillation gave the pure d-menthyl d-isomenthoxy acetate. b.p.=134°/0.3 mm. Found: C, 74.96; H, 11.41, Calc. for $C_{22}H_{40}O_3$; C, 74.95; H, 11.44%.

EXAMPLE 5

Preparation of d,l-Menthyl d-Isomenthoxyacetate

The procedure of Example 3 was repeated but with d,l-menthol (0.25 moles) as the reacting alcohol. GLC analysis of the crude product (78.5 g.) showed 88.4% ester and 9.5% d,l-menthol. Distillation gave the pure d,l-menthyl d-isomenthoxy acetate. b.p.=140°/0.35 mm. Found: C, 75.2; H, 11.37; Calc. for $C_{20}H_{40}O_3$; C, 74.95; H, 11.44%.

EXAMPLE 6

Preparation of N-Ethyl d-isomenthoxyacetamide d-Isomenthoxyacetic acid (0.12 moles) was added slowly to thionyl chloride (0.55 moles) while the temperature was slowly brought to 95° C. The reaction mixture was refluxed for 5 hours after which excess thionyl chloride was removed by distillation. An etherial solution of the acid chloride was added slowly to an etherial solution of ethylamine (0.36 moles) during which time the reaction mixture came to reflux. The reaction mixture was stirred for 1 hour and then washed with acid and base. Evaporation of the ether layer gave an oil (22.9 g.) which analyzed by GLC to be d-isomenthol, the ethylamide, and a minor unknown. Distillation of the reaction product gave the pure N-ethyl d-isomenthoxyacetamide (b.p.=125°/0.4 mm.) IR and NMR spectra were compatible with the amide.

We claim:
1. N-Ethyl d-isomenthoxyacetamide.
2. l-Menthyl d-isomenthoxy acetate.
3. d-Menthyl d-isomenthoxy acetate.
4. d,l-Menthyl d-isomenthoxy acetate.

* * * * *